US012599897B2

(12) United States Patent
Li et al.

(10) Patent No.: US 12,599,897 B2
(45) Date of Patent: *Apr. 14, 2026

(54) DIRECT CATALYTIC CONVERSION OF ALCOHOLS TO OLEFINS OF HIGHER CARBON NUMBER WITH REDUCED ETHYLENE PRODUCTION

(71) Applicant: UT-Battelle, LLC, Oak Ridge, TN (US)

(72) Inventors: Zhenglong Li, Shandong (CN); Brian H. Davison, Knoxville, TN (US); Junyan Zhang, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 11 days.

This patent is subject to a terminal disclaimer.

(21) Appl. No.: 18/198,899

(22) Filed: May 18, 2023

(65) Prior Publication Data

US 2023/0415132 A1 Dec. 28, 2023

Related U.S. Application Data

(63) Continuation of application No. 17/584,651, filed on Jan. 26, 2022, now Pat. No. 11,691,129.

(60) Provisional application No. 63/141,996, filed on Jan. 27, 2021.

(51) Int. Cl.
| | |
|---|---|
| *C07C 1/24* | (2006.01) |
| *B01J 21/08* | (2006.01) |
| *B01J 23/89* | (2006.01) |

(52) U.S. Cl.
CPC ............. *B01J 23/894* (2013.01); *B01J 21/08* (2013.01); *C07C 1/24* (2013.01); *C07C 2521/08* (2013.01); *C07C 2523/89* (2013.01)

(58) Field of Classification Search
CPC ............ C07C 1/24; B01J 23/894; B01J 21/08
See application file for complete search history.

(56) References Cited

U.S. PATENT DOCUMENTS

| | | | |
|---|---|---|---|
| 3,702,886 | A | 11/1972 | Argauer et al. |
| 4,427,789 | A | 1/1984 | Miale et al. |
| 4,596,704 | A | 6/1986 | Miale et al. |
| 4,721,609 | A | 1/1988 | Baacke et al. |
| 5,314,665 | A | 5/1994 | Iwasa |
| 7,438,868 | B2 | 10/2008 | Kato |
| 7,442,425 | B2 | 10/2008 | Fu et al. |
| 7,459,413 | B2 | 12/2008 | Shen et al. |
| 10,300,474 | B2 | 5/2019 | Li |
| 10,647,622 | B1 | 5/2020 | Dagle et al. |
| 10,647,625 | B2 | 5/2020 | Dagle et al. |
| 11,046,623 | B1 | 6/2021 | Dagle et al. |
| 11,053,181 | B2 | 7/2021 | Li |
| 11,292,753 | B2 | 4/2022 | Li |
| 2010/0029994 | A1 | 2/2010 | Manzer et al. |
| 2016/0082417 | A1 | 3/2016 | Lewandowski et al. |
| 2017/0217853 | A1 | 8/2017 | Lee et al. |
| 2018/0187091 | A1 | 7/2018 | Narula et al. |
| 2020/0048170 | A1 | 2/2020 | Li |
| 2020/0188882 | A1 | 6/2020 | Fraga et al. |

OTHER PUBLICATIONS

Dai et al. Zeolite Structural Confinement Effects Enhance One-Pot Catalytic Conversion of Ethanol to Butadiene. ACS Catalysis, vol. 7, 3703-3706. (Year: 2017).*
International Search Report and Written Opinion dated Jun. 1, 2022 issued in PCT/US 22/13801, 12 pages.

* cited by examiner

*Primary Examiner* — Sikarl A Witherspoon

(74) *Attorney, Agent, or Firm* — Scully, Scott, Murphy & Presser, P.C.

(57) ABSTRACT

A catalyst composition for converting an alcohol to olefins, the catalyst composition comprising the following components: (a) a support (e.g., particles) comprising silicon and oxygen; (b) at least one of copper and silver residing on and/or incorporated into said support; and (c) at least one lanthanide element residing on and/or incorporated into said support. The catalyst may also further include component (d), which is zinc. Also described herein is a method for converting an alcohol to one or more olefinic compounds (an olefin fraction) by contacting the alcohol with a catalyst at a temperature of at least 100° C. and up to 500° C. to result in direct conversion of the alcohol to an olefin fraction containing one or more olefinic compounds containing at least three carbon atoms; wherein ethylene and propylene are produced in a minor proportion of the olefin fraction, and butenes and higher olefins are produced in major proportion.

15 Claims, 6 Drawing Sheets

DIRECT CATALYTIC CONVERSION OF ALCOHOLS TO OLEFINS OF HIGHER CARBON NUMBER WITH REDUCED ETHYLENE PRODUCTION

CROSS REFERENCE TO RELATED APPLICATION

The present application is a continuation of U.S. patent application Ser. No. 17/584,651 filed on Jan. 26, 2022, which claims benefit of U.S. Provisional Application No. 63/141,996 filed on Jan. 27, 2021, all of the contents of which are incorporated herein by reference.

GOVERNMENT SUPPORT

This invention was made with government support under Prime Contract No. DE-AC05-00OR22725 awarded by the U.S. Department of Energy. The government has certain rights in the invention.

FIELD OF THE INVENTION

The present invention relates, generally, to the catalytic conversion of alcohols to hydrocarbons, and more particularly, to zeolite-based catalytic methods for conversion of alcohols, such as ethanol, to olefins.

BACKGROUND OF THE INVENTION

As part of a continuing effort in finding more cost-effective, environmentally friendly, and independent solutions to fuel production and consumption, the conversion of ethanol and other alcohols to hydrocarbons has become an active field of study. Ethanol, in particular, is of particular interest as an alcohol feedstock because it has the potential to be made in large quantity by renewable means (e.g., fermentation of biomass or syngas fermentation). However, several hurdles need to be overcome before such a process can become industrially feasible for producing olefins and hydrocarbon blendstocks of substantial equivalence to jet fuel, gasoline and other petrochemical fuels.

A few ethanol conversion technologies for jet fuel production are currently available. One approach is via ethanol dehydration to ethylene followed by two-step oligomerization to jet-range and gasoline-range hydrocarbons, and hydrogenation. This technology requires significant energy input due to the endothermic dehydration reaction. The ethylene oligomerization step is generally costly. Moreover, two steps are needed to convert ethanol to butene-rich olefins. The overall conversion involves four key steps: ethanol dehydration, ethylene dimerization, butene-rich olefin oligomerization, and hydrotreating. In addition, selective production of butene-rich olefins from ethylene over heterogeneous catalysts remains challenging due to substantial formation of side products (e.g., aromatics and light paraffins). To mitigate formation of such side products, the process is often operated at medium conversion of ethylene, which leads to an additional step of energy-intensive ethylene separation from light $C_3$-$C_4$ olefins. Lastly, this technology lacks the opportunity for generating a significant amount of diesel fuel and other high-value chemicals, which has higher value than either gasoline or jet fuel, and the demand of renewable diesel is also rapidly increasing. Another approach is to convert ethanol to isobutylene via a mixed oxide catalyst, followed by oligomerization and hydrogenation. A major limitation in the foregoing process is the low carbon efficiency due to a significant amount of carbon dioxide formation.

Acetone-butanol-ethanol (ABE) fermentation, a well-known commercial process, has recently regained significant interest for on-purpose n-butanol production. The ABE fermentation products are known to be important building blocks for middle distillate fuel (jet or diesel fuels) production. Direct dehydration of butanol is usually employed to produce butenes, which are then oligomerized to liquid hydrocarbon fuels containing primarily gasoline and jet-range hydrocarbons, and minor diesel range hydrocarbons due to low carbon number of butenes. The other fermentation products (e.g., ethanol) can be converted to ethylene, which is more challenging to convert to middle distillate fuels.

Another process for converting ABE to fuels is via cascade dehydrogenation, aldol condensation, alkylation reactions, followed by hydrogenation and hydrotreating reactions (*Nature*, 2012, 491, 235). Water poisoning and deactivating aldol condensation catalysts are well known, and water has been shown to inhibit the reported ABE to fuels reactions. Water separation from ABE fermentation products requires an energy-intensive separation process. The energy cost associated with ABE separation is substantial (~14%) for biological ABE production. Thus, there remains an as yet unrealized need to develop an ABE conversion technology that can mitigate the need for water removal and product separations. Similar challenges remain for other butanol to middle distillate conversion process. A few other challenges related to this technology include limited product yield and reliance on a high loading of precious metals (e.g., 5% Pd/C).

In view of the numerous disadvantages associated with currently known conversion processes, there would be a significant benefit in a process that could produce olefins (and ultimately, a synthetic fossil fuel) from alcohols with a higher carbon efficiency and at the same or lower cost than known in the art. There would be a particular advantage in such a process that could mitigate or avoid the costly endothermic ethanol dehydration step, the energy-intensive ethylene separation step, the overall number of steps, and the production of paraffins and aromatics.

SUMMARY OF THE INVENTION

The present disclosure is directed to catalysts useful in the conversion of alcohols to olefins, as well as methods for the conversion of alcohols to olefins by use of these catalysts. The catalysts described herein can produce olefins from alcohols with high carbon efficiency and at the same or lower cost than conventional methods. The present disclosure describes a more efficient and direct technology for converting ethanol to hydrocarbon fuels, particularly middle distillate hydrocarbon fuels. The process provides the following additional benefits: 1) avoids the additional endothermic ethanol dehydration step; 2) mitigates or avoids an energy-intensive ethylene separation step by significantly reducing ethylene production; 3) can reduce the number of key ethanol conversion steps from four or five to three, offering a great opportunity to reduce capital and operating expenses; and 4) can reduce or substantially eliminate formation of paraffins and aromatics during ethanol conversion, which offers the potential to increase the middle distillate yield.

The catalyst composition includes precisely or at least the following components: (a) a support (typically made of particles) containing at least silicon and oxygen atoms; (b) at least one of copper and silver atoms residing on and/or incorporated into the support; and (c) at least one lanthanide element (e.g., La, Ce, or higher atomic number lanthanide) residing on and/or incorporated into the support. In separate or further embodiments, the catalyst may further include zinc (Zn) residing on and/or incorporated into the support particles, integrated into or with component (b), or component (c), or integrated into or with both components (b) and (c). In some embodiments, all support particles have the same composition. In the foregoing scenario, a portion of the support particles may contain (i.e., residing thereon and/or incorporated therein) component (b) and not component (c), and a portion of the support particles may contain component (c) and not component (b), or alternatively, all support particles may contain component (b) and component (c). In other embodiments, the support particles include at least a first set of support particles and a second set of support particles having different compositions. In the foregoing scenario, the first set of support particles may contain component (b) and not component (c), and the second set of support particles may contain component (c) and not component (b), or alternatively, at least the first set of support particles and the second set of support particles contain component (b) and component (c). In separate or further embodiments, at least a portion of the support particles have a silica composition. In separate or further embodiments, at least a portion of the support particles include aluminum atoms and have a zeolite composition, wherein the zeolite composition may be partially dealuminated and have a silicon to aluminum ratio of at least or above 5 or 10, or the dealuminated zeolite composition may not contain aluminum (i.e., be completely dealuminated and composed of only silicon oxide and optionally one or more other elements in a trace amount). In separate or further embodiments, component (b) or component (c) is present by weight of support particles in an amount of 0.5-20 wt % or 0.5-30 wt %.

In the conversion method, the alcohol is contacted with any of the above-described catalyst compositions at a temperature of at least 100° C. and up to 500° C. to result in direct conversion of the alcohol to an olefin fraction comprising one or more olefinic compounds containing at least three or more carbon atoms. The method may also produce ethylene in an amount of no more than or less than 5 vol % in the olefin fraction. The method may alternatively or in addition produce propene in an amount of no more than or less than 25 vol % in the olefin fraction. The method may alternatively or in addition produce butenes in an amount of least or above 20, 25, or 30 vol % in the olefin fraction. In separate or further embodiments, alkanes (e.g., paraffins) are optionally produced along with the olefin fraction in an amount of no more than or less than 2 or 3 vol %. In separate or further embodiments, aromatics are optionally produced along with the olefin fraction in an amount of no more than or less than 1 or 2 vol %. In separate or further embodiments, olefins containing at least five carbon atoms are present in the olefin fraction in an amount of at least or above 20, 30, or 40 vol %. In separate or further embodiments, the alcohol has one to four carbon atoms, or the alcohol more specifically is or includes ethanol. In separate or further embodiments, the alcohol is in aqueous solution in a concentration of no more than 60, 50, 40, 30, or 20 vol %. In separate or further embodiments, the alcohol is a component of a fermentation stream, or more particularly, an acetone-butanol-ethanol (ABE) fermentation stream, 2,3-butanediol fermentation stream, or 1-butanol/isobutanol fermentation stream, when contacted with the catalyst.

In the process, ethanol is converted to higher olefins, e.g., butenes and hexenes, which can be readily converted to jet fuel or other synthetic fossil fuel with high carbon efficiency and low oligomerization cost. Moreover, the reactions proceed with negligible $CO_2$ formation. At the same time, the process is also amenable for producing 1,3-butadiene, which is a high value commodity chemical since it is used as a precursor for a number of applications, including in the production of rubber and plastics.

The new catalyst materials have the ability to convert either pure alcohols or aqueous solutions thereof into jet fuel and valuable co-products (e.g., 1,3-butadiene). In particular embodiments, the present disclosure is directed to a method for converting ethanol to liquid hydrocarbon fuels via 1) one-step ethanol conversion to $C_{3+}$ olefins with significant production of $C_{5+}$ olefins, 2) oligomerization, and 3) hydrotreating. In the first step, ethanol is converted to $C_{3+}$ olefins in one step without an ethanol dehydration step. This step may be achieved over a copper-modified Lewis acid catalyst, such as a Cu-modified La-based Beta zeolite (e.g., Cu—Zn—La/Beta or Cu/SiO$_2$-Zn/La/Beta). The present disclosure particularly demonstrates that ethanol can be converted to $C_{3+}$ olefins over three La-based catalysts, including Cu—Zn—La/Beta catalyst, Cu/SiO$_2$-Zn/La/Beta catalyst, and Cu/SiO$_2$-La/Beta at about 350° C. and ambient pressure under a hydrogen environment. Ethanol conversion of greater than 97% can be achieved with greater than 80% $C_{3+}$ olefins selectivity. The $C_{5+}$ olefins selectivity may be as high as 62% or higher. For the second step, the $C_{3+}$ olefins may be readily oligomerized to diesel-range or middle-distillate-range hydrocarbons over solid acid catalysts (e.g., zeolites) along with production of gasoline-range and jet-range hydrocarbons, or more particularly, production of jet and diesel fuels.

BRIEF DESCRIPTION OF THE DRAWINGS

FIG. 1A is a schematic of an exemplary process for converting ethanol or other alcohol to $C_{4+}$ olefins, or co-producing 1,3-butadiene, optionally followed by oligomerization and hydrogenation to form gasoline, diesel and jet fractions. FIG. 1B is a schematic of an exemplary process for converting butanol (such as from an ABE process) or other alcohol to $C_{4+}$ olefins, optionally followed by oligomerization and hydrogenation to form gasoline, diesel and jet fractions.

DETAILED DESCRIPTION OF THE INVENTION

Figures 1A, 1B:
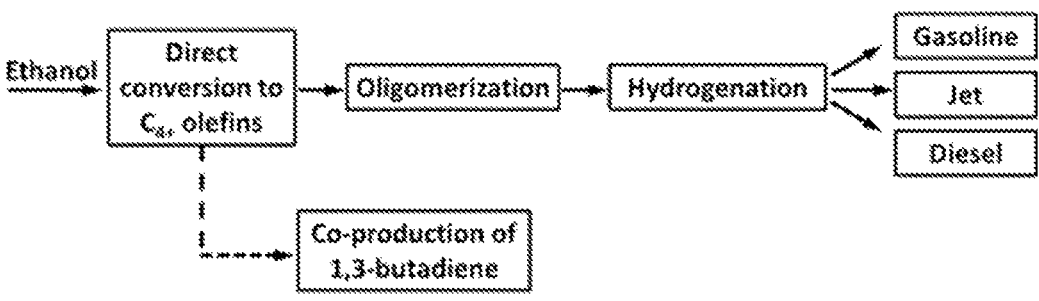
FIGS. 1A-1B.

In a first aspect, the present disclosure is directed to a catalyst composition useful for converting an alcohol to olefin compounds (i.e., olefin fraction). The catalyst composition includes or exclusively contains the following components: (a) support particles composed of at least silicon and oxygen atoms, (b) at least one of copper (Cu) and silver (Ag) atoms residing on and/or incorporated into the support particles, and (c) at least one lanthanide element residing on and/or incorporated into the support particles. In some embodiments, the catalyst further includes: (d) zinc atoms residing on and/or incorporated into the support particles, integrated into either component (a), or component (b), or integrated into both components (a) and (b).

In one set of embodiments, the support particles are silica particles, i.e., the support particles are composed of only silicon and oxygen atoms. The silica support particle may or may not contain a trace amount of one or more other elements (e.g., Al, Mg, Ca, K, Na, Fe, B, P, Zn, Cu, Ni, and/or Cd), typically in a total amount of no more than or less than 0.5, 0.2, 0.1, 0.01, 0.001, or 0.0001 wt %, depending on the purity.

In another set of embodiments, at least a portion or all of the support particles further include aluminum atoms and have a zeolite composition having any of the silicon to aluminum ratios disclosed earlier above or as set forth below. In other embodiments, at least a portion or all of the support particles have a zeolite composition after complete dealumination, i.e., with no aluminum present. The zeolite can be any of the porous aluminosilicate structures known in the art that are stable under high temperature conditions, i.e., of at least 100° C., 150° C., 200° C., 250° C., 300° C., and higher temperatures up to, for example, 500° C., 550° C., 600° C., 650° C., 700° C., 750° C., 800° C., 850° C., or 900° C. In particular embodiments, the zeolite is stable from at least 100° C. and up to 700° C. Typically, the zeolite is ordered by having a crystalline or partly crystalline structure. The zeolite can generally be described as a three-dimensional framework containing silicate ($SiO_2$ or $SiO_4$) and aluminate ($Al_2O_3$ or $AlO_4$) units that are interconnected (i.e., crosslinked) by the sharing of oxygen atoms.

In various embodiments, the zeolite (whether aluminated, partially dealuminated, or completely dealuminated) is a MFI-type zeolite, MWW-type zeolite, MEL-type zeolite, MTW-type zeolite, MCM-type zeolite, BEA-type zeolite, kaolin, or a faujasite-type of zeolite. Some particular examples of zeolites include the pentasil zeolites, and more particularly, the ZSM class of zeolites (e.g., ZSM-5, ZSM-8, ZSM-11, ZSM-12, ZSM-15, ZSM-23, ZSM-35, ZSM-38, ZSM-48), zeolite X, zeolite Y, zeolite beta (i.e., Beta zeolite or BEA), and the MCM class of zeolites (e.g., MCM-22 and MCM-49). The compositions, structures, and properties of these zeolites are well-known in the art, and have been described in detail, as found in, for example, U.S. Pat. Nos. 4,721,609, 4,596,704, 3,702,886, 7,459,413, and 4,427,789, the contents of which are incorporated herein by reference in their entirety. The zeolite can also have any suitable silica-to-alumina (i.e., $SiO_2/Al_2O_3$ or "Si/Al") ratio. For example, the zeolite can have a Si/Al ratio of precisely, at least, more than, less than, or up to 1, 2, 3, 4, 5, 6, 7, 8, 9, 10, 11, 12, 13, 14, 15, 20, 25, 30, 35, 40, 45, 55, 60, 65, 70, 75, 80, 85, 90, 95, 100, 120, 150, 200, 300, 400, or 500, or a Si/Al ratio within a range bounded by any two of the foregoing values. As aluminum is present in any of the foregoing zeolite compositions having any of the recited Si/Al ratios, any such zeolite is herein considered to be partially dealuminated. The zeolite may also be completely dealuminated, in which case the zeolite does not contain aluminum, and thus, cannot have a Si/Al ratio. In some embodiments, the zeolite is at least partially dealuminated and has a Si/Al ratio of at least or above 5, 10, 15, 20, 25, or 30, including any of the Si/Al ratios over delineated above. In some embodiments, the zeolite is a 2D pillared zeolite, as well known in the art. The 2D pillared zeolite can be a 2D pillared version of any of the zeolites described above, such as a pillared MFI or MWW zeolite.

In particular embodiments, the zeolite (whether aluminated, partially dealuminated, or completely dealuminated) is a Beta (BEA) zeolite. The BEA zeolite may possess any suitable Si/Al ratio, including any of the ratios provided above. For example, the BEA zeolite can have a Si/Al ratio of precisely, at least, more than, less than, or up to 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 120, 150, 200, 250, 300, 350, 400, 450, or 500, or a Si/Al ratio within a range bounded by any two of the foregoing values. As aluminum is present in any of the foregoing Beta zeolite compositions having any of the recited Si/Al ratios, any such zeolite is herein considered to be partially dealuminated. The Beta zeolite may also be completely dealuminated, in which case the Beta zeolite does not contain aluminum, and thus, cannot have a Si/Al ratio. Beta zeolite compositions having a Si/Al ratio of at least or greater than 100, 200, or 500 are particularly considered herein as dealuminated Beta zeolites. Notably, in some embodiments, a pure silica (no Al) Beta zeolite-type framework may be used. In some embodiments, the pure silica zeolite-type framework may also be a pillared zeolite.

In some embodiments, all support particles in the catalyst have the same composition, e.g., all silica, or all a particular zeolite, such as a Beta zeolite or ZSM (e.g., ZSM-5) zeolite. In other embodiments, at least two different types of support particles are present, e.g., silica admixed with zeolite (e.g., beta or ZSM zeolite) support particles, or at least two different types of zeolite support particles selected from any of the zeolite compositions provided earlier above, e.g., Beta zeolite admixed with a ZSM (e.g., ZSM-5) zeolite.

Any of the various types of support particles described above may have any of the particle sizes well known in the art. In different embodiments, the support particles have a size of precisely or about, for example, 0.1, 0.2, 0.5, 1, 2, 3, 4, 5, or 10 microns, or a particle size within a range bounded by any two of the foregoing values. In some embodiments, the particle size is substantially uniform, such as reflected in a deviation of no more than ±1, 2, or 10% from a particular size selected from the above exemplary values. In other embodiments, the particle size is substantially broad, such as reflected in a deviation of about or at least ±20, 30, 40, 50, or more from a particular size selected from the above exemplary values. The substantially broad particle size may also be characterized by monomodal, bimodal, trimodal, or higher modal distribution.

At least a portion of any of the types of support particles described above, including any of the silica or zeolite types of supports described above, contains component (b), wherein component (b) includes or exclusively contains at least one of copper (Cu) and silver (Ag) residing on and/or incorporated into the support particles. The Cu and/or Ag atoms are present in their ionic (non-metallic) state in component (b). In some embodiments, at least a portion or all of the support particles contain Cu atoms, with Ag atoms absent or present. In other embodiments, at least a portion or all of the support particles contain Ag atoms, with Cu atoms absent or present. In other embodiments, both Cu and Ag atoms are present in at least a portion or all of the support particles. In particular embodiments, the Cu and/or Ag atoms are present in silica support particles, and the silica support particles may or may not be in admixture with any of the zeolite support particles described above. In other particular embodiments, the Cu and/or Ag atoms are present in zeolite support particles, or more particularly, Beta zeolite support particles, and the zeolite support particles may or may not be in admixture with any of the silica support particles described above. Component (b) is typically present by weight of support particles in an amount of 0.5-20 wt %. In different embodiments, component (b) is present in an amount of precisely or about 0.5, 1, 2, 3, 4, 5, 6, 7, 8, 9, 10, 11, 12, 13, 14, 15, 16, 17, 18, 19, or 20 wt %, or an amount within a range bounded by any two of the foregoing values (e.g., 0.5-20 wt %, 0.5-15 wt %, 0.5-10 wt %, 1-20 wt %, 1-15 wt %, or 1-10 wt %).

At least a portion of any of the types of support particles described above, including any of the silica or zeolite types of supports described above, also contains component (c), wherein component (c) includes or exclusively contains at least one type of lanthanide element residing on and/or incorporated into the support particles. The lanthanide elements are present in their ionic (non-metallic) state in component (c). The term "lanthanide element" refers to any of the elements having an atomic number of 57-71, e.g., lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu). In particular embodiments, component (c) is or includes lanthanum and/or cerium. In particular embodiments, the lanthanide atoms are present in silica support particles, and the silica support particles may or may not be in admixture with any of the zeolite support particles described above. In other particular embodiments, the lanthanide atoms are present in zeolite support particles, or more particularly, Beta zeolite support particles, and the zeolite support particles may or may not be in admixture with any of the silica support particles described above. Component (c) is typically present by weight of support particles in an amount of 0.5-30 wt %. In different embodiments, component (c) is present in an amount of precisely or about 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 wt %, or an amount within a range bounded by any two of the foregoing values (e.g., 0.5-30 wt %, 0.5-25 wt %, 0.5-20 wt %, 0.5-15 wt %, 0.5-10 wt %, 1-30 wt %, 1-25 wt %, 1-20 wt %, 1-15 wt %, or 1-10 wt %).

In some embodiments, the catalyst further includes zinc (Zn) atoms, in their ionic state, residing on and/or incorporated into at least a portion of the support particles. In a first embodiment, the Zn ions are included in support particles also containing component (b). In a second embodiment, the Zn ions are included in support particles also containing component (c). In a third embodiment, the Zn ions are included in support particles also containing components (b) and (c).

In a first set of embodiments, all support particles have the same composition and all support particles contain component (b) and component (c). An example of such a catalyst is one in which all support particles have a silica composition and all silica support particles contain copper and lanthanum, or copper, lanthanum, and zinc. Another example of such a catalyst is one in which all support particles have a zeolite (e.g., Beta zeolite or ZSM-5 zeolite, typically partially or completely dealuminated) composition and all zeolite support particles contain copper and lanthanum, or copper, lanthanum, and zinc. Another example of such a catalyst is one in which all support particles have a silica composition and all silica support particles contain silver and lanthanum, or silver, lanthanum, and zinc. Another example of such a catalyst is one in which all support particles have a zeolite (e.g., Beta zeolite or ZSM-5 zeolite, typically partially or completely dealuminated) composition and all zeolite support particles contain silver and lanthanum, or silver, lanthanum, and zinc. Another example of such a catalyst is one in which all support particles have a silica composition and all silica support particles contain copper and cerium, or copper, cerium, and zinc. Another example of such a catalyst is one in which all support particles have a zeolite (e.g., Beta zeolite or ZSM-5 zeolite, typically partially or completely dealuminated) composition and all zeolite support particles contain copper and cerium, or copper, cerium, and zinc. Another example of such a catalyst is one in which all support particles have a silica composition and all silica support particles contain silver and cerium, or silver, cerium, and zinc. Another example of such a catalyst is one in which all support particles have a zeolite (e.g., Beta zeolite or ZSM-5 zeolite, typically partially or completely dealuminated) composition and all zeolite support particles contain silver and cerium, or silver, cerium, and zinc.

In a second set of embodiments, all support particles have the same composition and a first portion of the support particles contains (i.e., residing thereon and/or incorporated therein) component (b) and not component (c), and a second portion of the support particles contains component (c) and not component (b). An example of such a catalyst is one in which all support particles have a silica composition, and a first portion of the silica support particles contains only copper and/or silver, while a second portion of silica support particles contains only lanthanum and/or cerium. Another example of such a catalyst is one in which all support particles have a zeolite (e.g., Beta zeolite or ZSM-5 zeolite, typically partially or completely dealuminated) composition, and a first portion of the zeolite support particles contains only copper and/or silver, while a second portion of zeolite support particles contains only lanthanum and/or cerium. Another example of such a catalyst is one in which all support particles have a silica composition, and a first portion of the silica support particles contains only copper and zinc, while a second portion of silica support particles contains only lanthanum and/or cerium. Another example of such a catalyst is one in which all support particles have a zeolite (e.g., Beta zeolite or ZSM-5 zeolite, typically partially or completely dealuminated) composition, and a first portion of the zeolite support particles contains only copper and zinc, while a second portion of zeolite support particles contains only lanthanum and/or cerium. Another example of such a catalyst is one in which all support particles have a silica composition, and a first portion of the silica support particles contains only copper (or silver), while a second portion of silica support particles contains only lanthanum (or cerium) and zinc. Another example of such a catalyst is one in which all support particles have a zeolite (e.g., Beta zeolite or ZSM-5 zeolite, typically partially or completely dealuminated) composition, and a first portion of the zeolite support particles contains only copper (or silver), while a second portion of zeolite support particles contains only lanthanum (or cerium) and zinc.

In a third set of embodiments, the support particles include at least a first set of support particles and a second set of support particles having different compositions, and all support particles contain component (b) and component (c), wherein component (b) and/or (c) is the same or different for all support particles. An example of such a catalyst is one in which the first set of support particles has a silica composition and the second set of support particles has a zeolite (e.g., Beta zeolite or ZSM-5 zeolite, typically partially or completely dealuminated) composition, and the first and second sets of support particles contain copper and lanthanum, or copper, lanthanum, and zinc. Another example of such a catalyst is one in which the first set of support particles has a partially or completely dealuminated ZSM-5 zeolite composition and the second set of support particles has a partially or completely dealuminated Beta zeolite composition, and the first and second sets of support particles contain copper and lanthanum, or copper, lanthanum, and zinc. Another example of such a catalyst is one in which the first set of support particles has a silica composition and the second set of support particles has a zeolite (e.g., Beta zeolite or ZSM-5 zeolite, typically partially or completely dealuminated) composition, and the first and second sets of support particles contain copper and cerium, or copper, cerium, and zinc. Another example of such a catalyst is one in which the first set of support particles has a partially or completely dealuminated ZSM-5 zeolite composition and the second set of support particles has a partially or completely dealuminated Beta zeolite composition, and the first and second sets of support particles contain copper and cerium, or copper, cerium, and zinc. Another example of such a catalyst is one in which the first set of support particles has a silica composition and the second set of support particles has a zeolite (e.g., Beta zeolite or ZSM-5 zeolite, typically partially or completely dealuminated) composition, and the first and second sets of support particles contain silver and lanthanum, or silver, lanthanum, and zinc. Another example of such a catalyst is one in which the first set of support particles has a partially or completely dealuminated ZSM-5 zeolite composition and the second set of support particles has a partially or completely dealuminated Beta zeolite composition, and the first and second sets of support particles contain silver and lanthanum, or silver, lanthanum, and zinc. Another example of such a catalyst is one in which the first set of support particles has a silica composition and the second set of support particles has a zeolite (e.g., Beta zeolite or ZSM-5 zeolite, typically partially or completely dealuminated) composition, and the first and second sets of support particles contain silver and cerium, or silver, cerium, and zinc. Another example of such a catalyst is one in which the first set of support particles has a partially or completely dealuminated ZSM-5 zeolite composition and the second set of support particles has a partially or completely dealuminated Beta zeolite composition, and the first and second sets of support particles contain silver and cerium, or silver, cerium, and zinc.

In a fourth set of embodiments, the support particles include at least a first set of support particles and a second set of support particles having different compositions, and the first set of support particles contains component (b) and not component (c), and the second set of support particles contains component (c) and not component (b). An example of such a catalyst is one in which the first set of support particles has a silica composition and the second set of support particles has a zeolite (e.g., Beta zeolite or ZSM-5 zeolite, typically partially or completely dealuminated) composition, and the first set of support particles contains only copper and/or silver, while the second set of the support particles contains only lanthanum and/or cerium. Another example of such a catalyst is one in which the first set of support particles has a ZSM zeolite composition and the second set of support particles has a Beta zeolite composition, and the first set of support particles contains only copper and/or silver, while the second set of support particles contains only lanthanum and/or cerium. Another example of such a catalyst is one in which the first set of support particles has a silica composition and the second set of support particles has a zeolite (e.g., Beta zeolite or ZSM-5 zeolite, typically partially or completely dealuminated) composition, and the first set of support particles contains only copper (and/or silver) and zinc, while the second set of support particles contains only lanthanum and/or cerium. Another example of such a catalyst is one in which the first set of support particles has a ZSM zeolite composition and the second set of support particles has a Beta zeolite composition, and the first set of support particles contains only copper (and/or silver) and zinc, while the second set of support particles contains only lanthanum and/or cerium. Another example of such a catalyst is one in which the first set of support particles has a silica composition and the second set of support particles has a zeolite (e.g., Beta zeolite or ZSM-5 zeolite, typically partially or completely dealuminated) composition, and the first set of support particles contains only copper (and/or silver), while the second set of support particles contains only lanthanum (and/or cerium) and zinc. Another example of such a catalyst is one in which the first set of support particles has a ZSM zeolite composition and the second set of support particles has a Beta zeolite composition, and the first set of support particles contains only copper (and/or silver), while the second set of support particles contains only lanthanum (and/or cerium) and zinc.

Compositions pertaining to the catalyst, as described above, can be synthesized by methods well known in the art. The method may incorporate the metal ions homogeneously into the silica or zeolite support, which may include metal ions on surfaces of the zeolite. In particular embodiments, the catalyst described herein is prepared by a solid-state ion exchange method in which the silica or zeolite is physically mixed (e.g., by grinding) with one or more metal nitrate precursors, followed by calcining (e.g., at a temperature of 500-600° C.) for a suitable period of time (e.g., 1-12 hours). For purposes of the present invention, the zeolite being impregnated with nitrate precursors is typically a dealuminated zeolite. In other embodiments, the catalyst can be prepared by, first, treating the silica or zeolite (which may or may not be dealuminated) with one or more solutions containing salts of the metals to be loaded. The metal-containing solution may be contacted with the silica or zeolite such that the solution is absorbed into the silica or zeolite, preferably into the entire volume of the silica or zeolite. In one embodiment, the impregnating step is achieved by treating the silica or zeolite with a solution that contains all of the metals to be loaded. In another embodiment, the impregnating step is achieved by treating the silica or zeolite with two or more solutions, wherein the different solutions contain different metals or combinations of metals. Each treatment of the silica or zeolite with an impregnating solution corresponds to a separate impregnating step. Typically, when more than one impregnating step is employed, a drying and/or thermal treatment step is employed between the impregnating steps. The preparation of a number of types of zeolites, including pillared forms of two-dimensional zeolites, is described in, for example, W. J. Roth et al., *Chem. Rev.*, 114, 4807-4837, 2014, the contents of which are herein incorporated by reference.

In another aspect, the present disclosure is directed to a method for converting an alcohol to one or more olefinic compounds. In the conversion method described herein, an alcohol is catalytically converted to one or more olefinic compounds (i.e., one or more "olefins") by contacting the alcohol with a metal-loaded zeolite catalyst at a suitable temperature (e.g., at least 100° C. and up to 500° C.) to result in the alcohol being directly converted to the one or more olefins. The alcohol is contacted with the catalyst by feeding an alcohol feed material (which contains at least the alcohol, typically in aqueous solution) to any of the catalyst compositions described at a specified elevated temperature, as further described below. As used herein, the term "alcohol" refers to a single alcohol or a mixture of two or more alcohols. The term "olefinic compounds" (i.e., "olefins") refers primarily to alkenes (e.g., $C_3$-$C_{12}$), which includes mono-enes and dienes (e.g., 1,3-butadiene). In some embodiments, alkenes (olefins) are herein considered to be distinct from 1,3-butadiene, in which case the method may be considered to produce an alkene (olefinic) fraction along with co-production of a 1,3-butadiene fraction. Notably, the process is a direct conversion of the alcohol to the olefin fraction, wherein the term "direct" indicates that any of the catalyst compositions described above, whether alone or admixed with a co-catalyst, converts the alcohol in the absence of a separate intermediate or final step that relies on another catalyst to achieve the conversion.

The alcohol considered herein is generally of the formula R—OH, where R is typically a straight-chained or branched alkyl group having at least one or two carbon atoms and up to any number of carbon atoms, e.g., up to 3, 4, 5, or 6 carbon atoms. The alcohol is typically a primary or secondary alcohol. Some examples of suitable alcohols include methanol, ethanol, n-propanol, isopropanol, n-butanol, isobutanol, sec-butanol, tert-butanol, n-pentanol, isopentanol, and n-hexanol. In some embodiments, the alcohol feed (starting) material contains at least ethanol, or ethanol in combination with one or more of the alcohols provided above. In some embodiments, the alcohol feed excludes any one or more alcohols described above, such as methanol. In some embodiments, the alcohol feed includes or exclusively contains ethanol and/or alcohols with more carbon atoms than ethanol. The alcohol may also be or include a diol, such as ethylene glycol, propylene glycol, or 2,3-butanediol. The alcohol feed may or may not also be accompanied by one or more other oxygen-containing molecules, which may or may not also be converted to the one or more olefinic compounds by the catalyst described in the present disclosure. The one or more other oxygen-containing molecules may be, for example, acetone, acetaldehyde, acetoin, dimethyl ether, diethyl ether, and/or furfural. In some embodiments, any one or more of the oxygen-containing molecules listed above may be in a trace amount (e.g., no more than or less than 1 wt %) or excluded from the feed containing the alcohol.

In the feed material, the alcohol can be in any concentration, including pure (dry) alcohol, i.e., at or about 100% or in aqueous solution. In some embodiments, the alcohol is in aqueous solution in a concentration of no more than 50 vol %, 40 vol %, 30 vol %, 20 vol %, or 10 vol %. In some embodiments, the alcohol considered herein, to be converted to olefins, is one that can be produced by a fermentation process (i.e., a bio-alcohol). Most notable examples of bio-alcohols considered herein include ethanol, n-butanol, and isobutanol. In different embodiments, the alcohol is ethanol, butanol, or isobutanol, or a combination thereof, as commonly found in fermentation streams. In particular embodiments, the alcohol is an aqueous solution of alcohol (i.e., the alcohol is a component of an aqueous solution), such as found in fermentation streams.

The feed material may, in some embodiments, be a fermentation stream that includes one or more alcohols therein as a component. The fermentation stream may be directly contacted with the catalyst to convert at least the one or more alcohols therein to an olefin fraction. The fermentation stream may be, for example, an acetone-butanol-ethanol (ABE) fermentation stream, 1-butanol/isobutanol stream, or a 2,3-butanediol fermentation stream. In fermentation streams, the alcohol is typically in a concentration of no more than about 20% (vol/vol), 15%, 10%, or 5%, wherein the term "about" generally indicates within ±1%, 2%, 5%, or up to ±10% of the indicated value. The aqueous solution of alcohol may contain the alcohol in any of the foregoing amounts. In some embodiments, a fermentation stream or other alcoholic aqueous solution derived from a fermentation stream is directly contacted with the catalyst (typically, after filtration to remove solids) to effect the conversion of the alcohol in the fermentation stream. In other embodiments, the fermentation stream or other alcoholic aqueous solution is concentrated in alcohol (for example, of at least or up to 20%, 30%, 40%, or 50%) before contacting the fermentation stream with the catalyst. In yet other embodiments, alcohol in the fermentation stream or other alcoholic aqueous solution is selectively removed from the alcoholic aqueous solution, such as by distillation, to produce a substantially pure form of alcohol as the feedstock (e.g., a concentration of at least 90% or 95% of alcohol). In still other embodiments, the alcohol is completely dewatered into 100% alcohol before contacting with the catalyst.

The olefinic compounds herein produced by the catalytic conversion of alcohols generally include a range of alkenes (e.g., at least propene, butenes, and $C_5$-$C_{10}$ alkenes) and/or dienes (e.g., 1,3-butadiene, 1,3-hexadiene, or 1,5-hexadiene). The term "alkenes," as used herein, includes at least hydrocarbon compounds containing a single carbon-carbon double bond, and may or may not also include olefins with two or more carbon-carbon double bonds, e.g., 1,3-butadiene or 1,3,5-hexatriene. Some examples of alkenes containing four or more carbon atoms (i.e., $C_{4+}$ alkenes, or more specifically, $C_{4-10}$ alkenes) include 1-butene, 2-butene, 1-pentene, cis-2-pentene, trans-2-pentene, isopentene (3-methyl-1-butene), 1-hexene, cis-2-hexene, trans-2-hexene, cis-3-hexene, trans-3-hexene, isohexene (4-methyl-1-pentene), 3-methyl-1-pentene, 3,4-dimethyl-1-pentene, 1-heptene, isoheptene (5-methyl-1-hexene), 4-methyl-1-hexene, 1-octene, 2,4,4-trimethyl-1-pentene, 1-nonene, cis-3-nonene, trans-3-nonene, 1-decene, cis-4-decene, and trans-4-decene. The process described herein may also be capable of producing a minor fraction of alkenes having a carbon number greater than 10, i.e., $C_{10+}$ alkenes, such as $C_{11}$ and $C_{12}$ alkenes. Notably, although in some embodiments, non-olefin product (e.g., paraffins, aromatics, and/or aldehydes) may be produced alongside the olefin fraction, the olefin fraction typically represents at least or greater than 80, 85, 90, 95, 96, 97, 98, 99, or 100 vol % of the total product volume.

In the process, a suitable reaction temperature is employed during contact of the one or more alcohols with the catalyst. Generally, the reaction temperature is at least 100° C. and up to 500° C. In different embodiments, the reaction temperature is precisely or about, for example, 100° C., 125° C., 150° C., 175° C., 200° C., 225° C., 250° C., 275° C., 300° C., 325° C., 350° C., 375° C., 400° C., 425° C., 450° C., 475° C., or 500° C., or a temperature within a range bounded by any two of the foregoing exemplary temperatures, e.g., 100° C.-500° C., 200° C.-500° C., 300° C.-500° C., 350° C.-500° C., 400° C.-500° C., 100° C.-450° C., 200° C.-450° C., 250° C.-450° C., 300° C.-450° C., 100° C.-400° C., 200° C.-400° C., 300° C.-400° C., 100° C.-300° C., or 200° C.-300° C. Generally, ambient (i.e., normal atmospheric) pressure of about 1 atm is used in the method described herein. However, in some embodiments, an elevated pressure may be used. For example, in some embodiments, the pressure may be elevated to, for example, 1.5, 2, 3, 4, or 5 atm.

In some embodiments, the conversion process is conducted under a hydrogen gas atmosphere, in the substantial or complete absence of oxygen, and wherein the hydrogen gas may be present in an amount of at least 10, 20, 30, 40, 50, 60, 70, 80, 90, or 100 vol % of the atmosphere. The hydrogen gas may or may not be admixed with one or more inert gases (e.g., nitrogen and/or argon). In other embodiments, the conversion process is conducted under an inert or partial inert atmosphere.

Ethylene is typically produced in the above described process in an amount of no more than 5 vol % of the olefin fraction. In different embodiments, depending on, inter alia, the catalyst composition and processing temperature, ethylene can be produced in an amount of no more than or less than, for example, 5, 4.5, 4, 3.5, 3, 2.5, 2, 1.5, 1, 0.5, 0.2, or 0.1 vol %, or an amount within a range bounded by any two of the foregoing values (e.g., 0.1-5 vol % or 0.1-2 vol %). In some embodiments, ethylene is not produced.

Propene (propylene) is typically produced in the above described process in an amount of no more than 25 vol % of the olefin fraction. In different embodiments, depending on, inter alia, the catalyst composition and processing temperature, propene can be produced in an amount of no more than or less than, for example, 25, 20, 15, 10, 5, 2, or 1 vol %, or an amount within a range bounded by any two of the foregoing values (e.g., 1-25 vol %, 1-20 vol %, 1-15 vol %, or 1-10 vol %).

Butenes are typically produced in the above described process in an amount of least vol % of the olefin fraction. In different embodiments, depending on, inter alia, the catalyst composition and processing temperature, butenes may be produced in an amount of at least or greater than, for example, 20, 25, 30, 35, 40, 45, 50, 55, 60, 65, 70, 75, 80, 85, or vol %, or an amount within a range bounded by any two of the foregoing values (e.g., 20-vol %, 30-80 vol %, 40-80 vol %, 20-85 vol %, 30-85 vol %, 40-85 vol %, 20-90 vol %, 30-vol %, or 40-90 vol %).

Olefins containing at least three carbon atoms (i.e., $C_{3+}$ olefins) may be present in the olefin fraction in an amount of at least 10 vol %. In different embodiments, depending on, inter alia, the catalyst composition and processing temperature, $C_{3+}$ olefins may be produced in an amount of at least or greater than, for example, 10, 15, 20, 25, 30, 35, 40, 45, 50, 55, 65, 70, 75, 80, 85, 90, 95, 96, 97, or 98 vol %, or an amount within a range bounded by any two of the foregoing values (e.g., 10-98 vol %, 20-98 vol %, 30-98 vol %, 40-98 vol %, vol %, 60-98 vol %, 70-98 vol %, and 80-98 vol %).

Olefins containing at least four carbon atoms (i.e., $C_{4+}$ olefins) may be present in the olefin fraction in an amount of at least 10 vol %. In different embodiments, depending on, inter alia, the catalyst composition and processing temperature, $C_{4+}$ olefins may be produced in an amount of at least or greater than, for example, 10, 15, 20, 25, 30, 35, 40, 45, 50, 55, 65, 70, 75, 80, 85, 90, 95, 96, 97, or 98 vol %, or an amount within a range bounded by any two of the foregoing values (e.g., 10-98 vol %, 20-98 vol %, 30-98 vol %, 40-98 vol %, vol %, 60-98 vol %, 70-98 vol %, and 80-98 vol %).

Olefins containing at least five carbon atoms (i.e., $C_{5+}$ olefins) may be present in the olefin fraction in an amount of at least 5 vol %. In different embodiments, depending on, inter alia, the catalyst composition and processing temperature, $C_{5+}$ olefins may be produced in an amount of at least or greater than, for example, 5, 10, 15, 20, 25, 30, 35, 40, 45, 50, 55, 65, or 70 vol %, or an amount within a range bounded by any two of the foregoing values (e.g., 5-50 vol %, 10-50 vol %, 5-40 vol %, 10-40 vol %, 5-30 vol %, and 10-30 vol %).

Olefins containing at least six carbon atoms (i.e., $C_{6+}$ olefins) may be present in the olefin fraction in an amount of at least 3 vol %. In different embodiments, depending on, inter alia, the catalyst composition and processing temperature, $C_{6+}$ olefins may be produced in an amount of at least or greater than, for example, 3, 4, 5, 10, 15, 20, 25, 30, 35, 40, 45, 55, 60, 65, or 70 vol %, or an amount within a range bounded by any two of the foregoing values (e.g., 3-50 vol %, 4-50 vol %, 5-50 vol %, 3-40 vol %, 4-40 vol %, 5-40 vol %, 3-30 vol %, 4-30 vol %, 5-30 vol %, 3-20 vol %, 4-20 vol %, 5-20 vol %, 3-10 vol %, 4-10 vol %, or 5-10 vol %).

Olefins containing at least seven carbon atoms (i.e., $C_{7+}$ olefins) may be present in the olefin fraction in an amount of at least 1 vol %. In different embodiments, depending on, inter alia, the catalyst composition and processing temperature, $C_{7+}$ olefins may be produced in an amount of at least or greater than, for example, 1, 2, 3, 4, 5, 10, 15, 20, 25, 30, 35, 40, 50, 55, 60, 65, or 70 vol %, or an amount within a range bounded by any two of the foregoing values (e.g., 1-40 vol %, 2-40 vol %, 3-40 vol %, 4-40 vol %, 5-40 vol %, 1-30 vol %, 2-30 vol %, 3-30 vol %, 4-30 vol %, 5-30 vol %, 1-20 vol %, 2-20 vol %, 3-20 vol %, 4-20 vol %, 5-20 vol %, 1-10 vol %, 2-10 vol %, 3-10 vol %, 4-10 vol %, or 5-10 vol %).

Olefins containing at least eight carbon atoms (i.e., $C_{8+}$ olefins) may be present in the olefin fraction in an amount of at least 1 vol %. In different embodiments, depending on, inter alia, the catalyst composition and processing temperature, $C_{8+}$ olefins may be produced in an amount of at least or greater than, for example, 1, 2, 3, 4, 5, 10, 15, 20, 25, 30, 35, 40, or 50 vol %, or an amount within a range bounded by any two of the foregoing values (e.g., 1-30 vol %, 2-30 vol %, 3-30 vol %, 4-30 vol %, 5-30 vol %, 1-20 vol %, 2-20 vol %, 3-20 vol %, 4-20 vol %, 5-20 vol %, 1-10 vol %, 2-10 vol %, 3-10 vol %, 4-10 vol %, 5-10 vol %, 1-5 vol %, 2-5 vol %, or 1-3 vol %).

Alkanes (e.g., ethane, propane, butanes, pentanes, and paraffins) may or may not be produced in the process described above along with the olefin fraction. If alkanes (or specifically, paraffins) are also produced, they are typically present in an amount of no more than 5 vol % of the total volume of products produced (i.e., wherein total products includes olefins and non-olefins). In different embodiments, depending on, inter alia, the catalyst composition and processing temperature, alkanes (or more specifically, paraffins) may be produced in an amount of no more than or less than, for example, 1, 2, 3, 4, or 5 vol %, or an amount within a range bounded by any two of the foregoing values (e.g., 1-5 vol %, 1-4 vol %, 1-3 vol %, or 1-2 vol %).

Aromatics (e.g., benzene, toluenes, and/or xylenes) may or may not be produced in the process described above along with the olefin fraction. If aromatics are also produced, they are typically present in an amount of no more than 2 vol % of the total volume of products produced (i.e., wherein total products includes olefins and non-olefins). In different embodiments, depending on, inter alia, the catalyst composition and processing temperature, aromatics may be produced in an amount of no more than or less than, for example, 0.1, 0.2, 0.5, 1, 1.5, or 2 vol %, or an amount within a range bounded by any two of the foregoing values (e.g., 0.1-2 vol %, 0.1-1 vol %, or 0.1-0.5 vol %).

Oxygenated product may or may not also be produced in the process described above along with the olefin product. The oxygenated product may be or include, for example, one or more aldehydes (e.g., acetaldehyde, propionaldehyde, and/or butyraldehyde) or ketones (e.g., acetone, butanones, pentanones, and diones). If oxygenated product is also produced, it is typically present in an amount of no more than 3 vol % of the total volume of products produced (i.e., wherein total volume of products includes olefins and non-olefins). In different embodiments, depending on, inter alia, the catalyst composition and processing temperature and atmosphere, oxygenated product may be produced in an amount of no more than or less than, for example, 0.1, 0.2, 0.5, 1, 1.5, 2, 2.5, or 3 vol %, or an amount within a range bounded by any two of the foregoing values (e.g., 0.1-3 vol %, 0.1-2 vol %, 0.1-1 vol %, or 0.1-0.5 vol %).

The catalyst and reactor can have any of the designs known in the art for catalytically treating a fluid or gas at elevated temperatures, such as a fluidized bed reactor. The process may be in a continuous or batch mode. In particular embodiments, the alcohol-containing feed is injected into a heated reactor such that the alcohol is quickly volatilized into gas, and the gas passed over the catalyst. In some embodiments, the reactor design includes a boiler unit and a reactor unit if the fermentation stream is used directly as a feedstock without purification. The boiler unit is generally not needed if the fermentation stream is distilled to concentrate ethanol because the distillation process removes the dissolved solids in the fermentation streams. The boiler unit volatilizes liquid feedstock into gases prior to entry into the reactor unit and withholds dissolved solids.

To effect further conversion of the olefins to a fossil fuel (e.g., a jet fuel), the olefinic compounds may be reacted with one or more additional catalysts known in the art capable of such transformation, such as oligomerization. The additional catalyst may be, for example, a zeolite (e.g., H-BEA, H-ZSM-5, MCM, H-ZSM-22, or H-ZSM-57), amorphous aluminosilicate, sulfonic acid ion-exchange resin (e.g., Amberlyst® 15, Amberlyst® 35, Amberlyst® 36, Purolite®, Dowex®, Lewatit®), or solid phosphoric acid. The conditions of the reaction may be, for example, 100-500° C. (or more particularly, 70-350° C.), 1-60 atm, a weight hourly space velocity (WHSV) of 0.1 $h^{-1}$ to 20 $h^{-1}$, and an inert or hydrogen carrier gas. The foregoing catalysts and conditions are generally suited for a dimerization, oligomerization, or dehydrocyclization process. However, the process may also include a hydrogenation (hydrotreating) process, which may employ an oxide catalyst (e.g., $Al_2O_3$, $TiO_2$, $CeO_2$, or $ZrO_2$) coated or impregnated with platinum (Pt), nickel (Ni), rhodium (Rh), ruthenium (Ru) or other noble metal or precious metal. In some embodiments, the oligomerization and hydrogenation occur simultaneously, while in other embodiments, the hydrogenation is performed after the oligomerization.

In some embodiments, the method converts an alcohol to a hydrocarbon fuel, such as jet fuel and/or diesel fuel, by: (i) producing the one or more olefinic compounds (olefin fraction) according to the method described above, (ii) oligomerizing the olefinic compounds to produce an oligomerized product, and (iii) hydrogenating (hydrotreating) the oligomerized product. Oligomerization and hydrogenation catalysts for effecting steps (ii) and (iii), respectively, are well known in the art.

The oligomerization process may more particularly entail, e.g., contacting the olefin fraction with an oligomerization catalyst at a temperature of at least 40° C. and up to 400° C. to result in an oligomerized product, e.g., a $C_6^+$, $C_7^+$, or $C_8^+$ partially unsaturated fraction. In different embodiments, step (ii) employs a temperature of precisely or about, for example, 50° C., 60° C., 70° C., 80° C., 90° C., 100° C., 150° C., 200° C., 250° C., 300° C., 350° C., or 400° C., or a temperature within a range bounded by any two of the foregoing values, e.g., 40-350° C., 40-300° C., 40-250° C., 40-200° C., 40-150° C., 50-400° C., 50-350° C., 50-300° C., 50-250° C., 50-200° C., 50-150° C., 80-400° C., 80-350° C., 80-300° C., 80-250° C., 80- 200° C., or 80-150° C. Oligomerization catalysts are well known in the art, as evidenced in, for example, A. Lacarriere et al., *ChemSusChem,* 5, 1787-1792 (2012), the contents of which are herein incorporated by reference. As well known, oligomerization catalysts can be divided into two main categories: acid catalysts, particularly suited for the oligomerization of $C_3$ or higher olefins, and nickel-containing catalysts (e.g., nickel complexes or nickel-exchanged zeolite), particularly suited for ethylene oligomerization. Some examples of oligomerization catalysts include acid zeolite catalysts (e.g., H-BEA, H-ZSM-5, MCM-41, H-ZSM-22, or H-ZSM-57), metal-containing zeolite catalysts (e.g., nickel- and aluminum-exchanged zeolites, such as NiMCM-41, AlMCM-41, NiMCM-48, and AlMCM-48), amorphous aluminosilicate, sulfonic acid ion-exchange resins (e.g., Amberlyst® 15, Amberlyst® 35, Amberlyst® 36, Purolite®, Dowex®, Lewatit®), sulfated alumina, and solid phosphoric acid. The oligomerization process may employ standard pressure (about 1 atm) or an elevated pressure (e.g., at least or above 10, 20, 30, or 50 atm). The oligomerization process may be conducted under an inert gas atmosphere. At the completion of or during the oligomerization process in step (ii), the second paraffin fraction and $C_7^+$ partially unsaturated (oligomeric) fraction are separated from each other by means well known in the art, and the first and second paraffin fractions are combined to result in a total $C_3$-$C_6$ paraffin fraction.

The hydrogenation process may more particularly entail, e.g., contacting the partially unsaturated fraction with a precious metal-containing hydrogenation catalyst in the presence of hydrogen gas at a temperature of at least 100° C. and up to 500° C. (or precisely or about 100° C., 150° C., or 200° C. and up to precisely or about 250° C., 300° C., 350° C., 400° C., 450° C., 500° C.) to produce a jet fuel or diesel hydrocarbon fraction, wherein the jet fuel or diesel hydrocarbon fraction contains a $C_6^+$, $C_7^+$, or $C_8^+$ paraffin fraction with substantially no olefin or aromatic fraction. Precious metal-containing hydrogenation catalysts are well known in the art, e.g., Pt or Pd on an oxide support, such as alumina ($Al_2O_3$). The hydrotreating process may employ standard pressure (about 1 atm) or an elevated pressure (e.g., at least or above 1, 2, 5, 10, 20, 30, 40, or 50 atm, or a range therein, e.g., 1-5 atm, 2-5 atm, 1-10 atm, 2-10 atm, 1-30 atm, or 2-30 atm), and may be conducted under a standard air atmosphere or an inert gas (e.g., nitrogen or argon) atmosphere. In some embodiments, the paraffin fraction includes or exclusively contains alkanes having at least eight, nine, or ten carbon atoms and up to twelve, fourteen, sixteen, eighteen, or twenty carbon atoms, e.g., a range of $C_8$-$C_{20}$, $C_8$-$C_{18}$, $C_8$-$C_{16}$, $C_8$-$C_{14}$, $C_9$-$C_{20}$, $C_9$-$C_{18}$, $C_9$-$C_{16}$, $C_9$-$C_{14}$, $C_{10}$-$C_{20}$, $C_{10}$-$C_{18}$, $C_{10}$-$C_{16}$, or $C_{10}$-$C_{14}$ alkanes.

The method described above produces a mainly liquid hydrocarbon fuel. Such fuel refers to a mixture of hydrocarbon compounds useful as a fuel or as a blendstock in a fuel. The mixture of hydrocarbon compounds produced herein substantially corresponds (e.g., in composition and/or properties) to a known petrochemical fuel, such as petroleum, or a fractional distillate of petroleum. Some examples of petrochemical fuels include jet fuel (i.e., jet propellant, such as JP-8), gasoline, kerosene, and diesel. Although aromatics (particularly benzene) may be present in the hydrocarbon mixture, their presence may be minimized by methods known in the art to adhere to current fuel standards. The raw hydrocarbon product may also be fractionated by distillation into different fuel grades, each of which is known to be within a certain boiling point range. Another advantage of the above described method is its ability to produce such fuel grades in the substantial absence of contaminants (e.g., mercaptans) normally required to be removed during the petroleum refining process. Moreover, by appropriate adjustment of the catalyst and processing conditions, a select distribution of hydrocarbons can be obtained.

Any of the catalysts described above can also be mixed with or affixed onto a support material suitable for the conditions of the conversion reaction. The support material may be a powder (e.g., having any of the above particle sizes), granular particles (e.g., 0.5 mm or greater particle size), a bulk material, such as a honeycomb monolith of the flow-through type, a plate or multi-plate structure, or corrugated metal sheets. If a honeycomb structure is used, the honeycomb structure can contain any suitable density of cells. For example, the honeycomb structure can have 100, 200, 300, 400, 500, 600, 700, 800, or 900 cells per square inch (cells/in$^2$) (or from 62-140 cells/cm$^2$) or greater. The support material is generally constructed of a refractory composition, such as those containing cordierite, mullite, alumina (e.g., $\alpha$-, $\beta$-, or $\gamma$-alumina), or zirconia, or a combination thereof. Honeycomb structures, in particular, are described in detail in, for example, U.S. Pat. Nos. 5,314,665, 7,442,425, and 7,438,868, the contents of which are incorporated herein by reference in their entirety. When corrugated or other types of metal sheets are used, these can be layered on top of each other with catalyst material supported on the sheets such that passages remain that permit the flow of the liquid or gas containing the organic species undergoing conversion. The layered sheets can also be formed into a structure, such as a cylinder, by winding the sheets.

Depending on the final composition of the hydrocarbon product, the product can be directed to a variety of applications, including, for example, as precursors for plastics, polymers, and fine chemicals. The process described herein can advantageously produce a range of olefin and non-olefin compounds that differ in any of a variety of characteristics, such as molecular weight (i.e., hydrocarbon weight distribution), degree of saturation or unsaturation (e.g., alkane to alkene ratio), and level of branched or cyclic isomers. The process provides this level of versatility by appropriate selection of, for example, composition of the catalyst, amount of catalyst (e.g., ratio of catalyst to alcohol precursor), processing temperature, atmosphere composition, and flow rate (e.g., LHS V).

In some embodiments, the conversion method described above is integrated with a fermentation process, wherein the fermentation process produces the alcohol used as feedstock for the conversion process. In one embodiment, the fermentation process is a biomass fermentation process that produces mainly ethanol or ethanol in combination with butanol from starches and sugars. In another embodiment, the fermentation process is a acetone-butanol-ethanol (ABE) fermentation process, as well known in art. In another embodiment, the fermentation process is a 2,3-butanediol process (which may also produce acetoin), as well known in the art. By being "integrated" is meant that alcohol produced at a fermentation facility or zone is sent to and processed at a conversion facility or zone that performs the conversion process described above. Preferably, in order to minimize production costs, the fermentation process is in close enough proximity to the conversion facility or zone, or includes appropriate conduits for transferring produced alcohol to the conversion facility or zone, thereby not requiring the alcohol to be shipped. In particular embodiments, the fermentation stream produced in the fermentation facility is directly transferred to the conversion facility, generally with removal of solids from the raw stream (generally by filtration or settling) before contact of the stream with the catalyst.

In some embodiments, the fermentation process is performed in an autonomous fermentation facility, i.e., where saccharides, produced elsewhere, are loaded into the fermentation facility to produce alcohol. In other embodiments, the fermentation process is part of a larger biomass reactor facility, i.e., where biomass is decomposed into fermentable saccharides, which are then processed in a fermentation zone. Biomass reactors and fermentation facilities are well known in the art. Biomass generally refers to lignocellulosic matter (i.e., plant material), such as wood, grass, leaves, paper, corn husks, sugar cane, bagasse, and nut hulls. Generally, biomass-to-ethanol conversion is performed by 1) pretreating biomass under well-known conditions to loosen lignin and hemicellulosic material from cellulosic material, 2) breaking down cellulosic material into fermentable saccharide material by the action of a cellulase enzyme, and 3) fermentation of the saccharide material, typically by the action of a fermenting organism, such as suitable yeast, to produce one or more alcohols.

In other embodiments, the alcohol is produced from a more direct sugar source, such as a plant-based source of sugars, such as sugar cane or a grain starch (such as corn starch). Ethanol production via corn starch (i.e., corn starch ethanol) and via sugar cane (i.e., cane sugar ethanol) currently represent some of the largest commercial production methods of ethanol. Integration of the instant conversion process with any of these large scale ethanol production methods is contemplated herein.

Examples have been set forth below for the purpose of illustration and to describe certain specific embodiments of the invention. However, the scope of this invention is not to be in any way limited by the examples set forth herein.

EXAMPLE 1

A method is described below for converting ethanol to liquid hydrocarbon fuels, in which the method includes one-step ethanol conversion to $C_{3+}$ and/or $C_{4+}$ olefins with significant $C_{5+}$ olefins. The method may co-produce 1,3-butadiene, and may optionally be followed by oligomerization and hydrogenation to form gasoline, diesel and jet fractions, as shown in FIG. 1A.

In the first step, ethanol is converted to $C_{3+}$ olefins in one step without ethanol dehydration step. This step is achieved by use of a copper-modified Lewis acid catalyst, e.g., a Cu-modified La-based Beta zeolite (e.g., Cu—Zn—La/Beta) or Cu/SiO$_2$-Zn/La/Beta. Particularly demonstrated herein is ethanol conversion to $C_{3+}$ olefins over three La-based catalysts, including Cu—Zn—La/Beta catalyst, Cu/SiO$_2$-Zn/La/Beta catalyst, and Cu/SiO$_2$-La/B eta at 350° C. and ambient pressure under a hydrogen environment. Ethanol conversion of >97% was achieved with >80% $C_{3+}$ olefins selectivity. $C_{5+}$ olefins selectivity can be as high as ca. 62% or higher. For the second step, these $C_{3+}$ olefins can be readily oligomerized to middle distillate-range hydrocarbons over solid acid catalysts, e.g., zeolites. The results are shown in Table 1 below.

TABLE 1

| One-step catalytic conversion of ethanol over La-based catalysts | | | |
| --- | --- | --- | --- |
| | Cu/SiO$_2$—La/BEA | Cu/SiO$_2$—Zn/La/BEA | Cu—Zn—La/BEA |
| Temperature (° C.) | | 350 | |
| Weight of catalyst (g) | 0.3005 | 0.3032 | 0.3036 |
| Ethanol flow rate (mL/h) | 0.2015 | 0.2015 | 0.2015 |
| H$_2$ flow rate (mL/h) | 18.6 | 18.6 | 18.6 |
| WHSV (h$^{-1}$) | 0.53 | 0.52 | 0.52 |
| H$_2$ concentration (%) | 93.1 | 93.1 | 93.1 |
| Ethanol concentration (%) | 6.9 | 6.9 | 6.9 |
| Acetaldehyde selectivity (%) | 12.4 | 1.9 | 4.9 |
| Ethylene selectivity (%) | 2.1 | 2.9 | 4.2 |
| Propene selectivity (%) | 0.4 | 1.1 | 1.8 |
| Butenes selectivity (%) | 25 | 31.7 | 37.6 |
| C$_{5+}$ olefins selectivity (%) | 54.6 | 61.9 | 48.8 |
| Total olefins selectivity (%) | 82.2 | 97.6 | 92.4 |
| Oxygenates selectivity (%) | 17.5 | 1.9 | 7.2 |
| Paraffins selectivity (%) | 0.4 | 0.5 | 0.4 |
| C$_{3+}$ olefins selectivity (%) | 80.1 | 94.7 | 88.2 |

$^a$Carbon selectivity

The method is also directed to conversion of ABE or butanol to liquid hydrocarbon fuels in which the method includes one-pot ABE conversion to C$_{3+}$ olefins. The method may further include oligomerization followed by hydrotreating, as shown in FIG. 1B.

In the first step, ABE or butanol is converted to C$_{3+}$ olefins in one pot without separating acetone, butanol, and ethanol and without complete removal of water from the fermentation broth. This step is achieved by use of a copper-modified Lewis acid catalysts, e.g., Cu-modified La-based Beta zeolite (e.g., Cu—Zn—La/Beta or Cu/SiO$_2$—Zn/La/Beta). Particularly demonstrated herein is ABE conversion to C$_{3+}$ olefins over Cu—Zn—La/BEA catalyst at 350° C. and ambient pressure under a hydrogen environment, wherein ca. 99.8% conversion of ABE is achieved with ca. 97% C$_{3+}$ olefins selectivity and ca. 43.5% C$_{5+}$ olefins, 26.5% C$_{7+}$ olefins. For the second step, these C$_{5+}$ olefins (especially C$_{7+}$ olefins) can be readily oligomerized to middle distillate-range hydrocarbons over solid acid catalysts, e.g., zeolites. The results are shown in Table 2 below.

TABLE 2

| One-step catalytic conversion of Acetone-Butanol-Ethanol (3:6:1, mass ratio) over Cu—Zn—La/BEA catalysts | |
| --- | --- |
| | Cu—Zn—La/BEA |
| Temperature (° C.) | 350 |
| Carrier gas | H$_2$ |
| Conversion (%) | 99.82 |
| Ethylene Sel (%) | 0.62 |
| Propene Sel (%) | 19.43 |
| Butenes Sel (%) | 34.24 |
| C$_5$ Olefins Sel (%) | 11.45 |
| C$_6$ Olefins Sel (%) | 5.56 |
| C$_{7+}$ Olefins Sel (%) | 26.51 |
| C$_{5+}$ Olefins Sel (%) | 43.53 |
| Total Olefins Sel (%) | 97.82 |
| Oxygenates Sel (%) | 1.12 |
| Paraffins Sel (%) | 1.24 |
| C$_{3+}$ olefins Sel (%) | 97.2 |

$^a$Carbon selectivity

The catalyst and method described herein for converting ethanol to C$_{3+}$ olefins offers numerous benefits, including: 1) avoidance of the additional endothermic ethanol dehydration step; 2) avoidance of energy-intensive ethylene separation step by significantly reducing ethylene production; 3) reduction in the number of key ethanol conversion steps from four/five to three, offering a great opportunity for reduction of CapEx and OpEx; 4) minimization of light paraffins formation and avoidance of aromatics formation during the ethanol conversion step, which offers the potential to increase the liquid hydrocarbon fuel yield. Moreover, ethanol can be directly converted to C$_{4+}$ olefins with high selectivity of C$_6$ and C$_8$ olefins. These olefin mixtures can be oligomerized to middle-range distillate fuels with the option to produce a higher fraction of jet or diesel fuel.

The catalyst and method described herein also provides a single-step ABE or butanol conversion to C$_{3+}$ olefins with >40% C$_{5+}$ olefins and significant amount of C$_{7+}$ olefins, which can be readily upgraded to jet or diesel-range hydrocarbons via oligomerization. This technology permits direct feeding of aqueous ABE streams without the need for removal of water and separation of ABE products, and this dramatically reduces the cost of the conversion process. The method can also provide substantially improved product yields. An added benefit is that the ABE conversion step is achieved using inexpensive earth-abundant catalysts, as described above, and this will help the process become cost-competitive with distillate fossil fuel production. The method can also advantageously be used for converting butanol or butanol fermentation mixture to middle distillate fuels.

Example 1. Cu—Ce/Beta Catalyst for Ethanol Conversion to Olefins

Cu—Ce/Beta Catalyst Synthesis

H-BEA (SAR=11.5) was obtained by calcinating NH$_4$-Beta (CP814E, Zeolyst) under 823 K under 1.7 cm$^3$ g$^{-1}$cat s$^{-1}$ air for 12 h. 10 g H-Beta was mixed with 250 mL nitric acid (69% to 70%) in a sealed container at 353 K with 500 rpm stirring for 16 h. The solid was centrifuged and washed with DI water until pH is close to 9. The washed powder was dried under 353 K in an oven overnight to remove the remaining water and acid. The sample was labeled as DeAl-Beta as the support for metal loading.

DeAl-Beta was mixed with copper nitrate trihydrate and cerium nitrate hexahydrate in the mortar and ground for 20 min. The mixed powder was homogeneous light green with no blue dots. The mixture was calcinated to 823 K with 1 K/min ramping rate and held for 6 h under 13.3 cm$^3$ g$^{-1}$cat s$^{-1}$ air to allow a complete decomposition of metal precursors and homogeneous distribution of metal species. The as-synthesized catalysts have 1 wt % Cu loading, along with 7 wt % and 11.6 wt % Ce loading, and have a light yellow color. The notation "7Ce" and "11.6Ce" is used herein as a shorthand to denote 7 wt % and 11.16 wt % of Ce in the catalyst. The catalysts produced in this experiment may then be expressed as Cu-7Ce/Beta and Cu-11.6Ce/Beta.

Cu—Ce/Beta Catalyst Testing

The reaction was carried out in a tubular quartz reactor with a fixed-bed configuration in a vertical tubular furnace. Typically, 0.3 g catalysts were treated in situ by heating at 5 K min$^{-1}$ to 673 K and for 1 h under 1.2 cm$^3$ g$^{-1}$cat s$^{-1}$ He to remove adsorbed species. After cooling down to 623 K, the catalyst was reduced under 1.44 cm$^3$ g$^{-1}$cat s$^{-1}$ pure H$_2$ for 30 min. Flow rates of He and H$_2$ were controlled using mass flow controllers. Ethanol was delivered using syringe pumps and were evaporated inside the $\frac{1}{8}$" stainless steel transfer lines. The types and the concentrations of the reactants and the products in stream were measured by a gas-chromatograph with thermal conductivity detector (TCD) and a flame ionization detector (FID). A gas chromatograph mass-spectrometer (GC-MS) was used to determine the peak position of reactants and products.

Catalytic Performance

More than 97% ethanol conversion was observed over both Cu-7Ce/Beta and Cu-11.6Ce/Beta catalysts at 623 K, ethanol weight hourly space velocity (WHSV) of 0.52 h$^{-1}$, 7.1 kPa ethanol balanced with H$_2$ (total pressure 101.3 kPa). The primary products were butenes and C$_{5+}$ olefins with a very small amount of propene. The selectivities of total C$_{3+}$ olefins were 82% and 81% for Cu-7Ce/Beta and Cu-11.6Ce/

Figure 3:
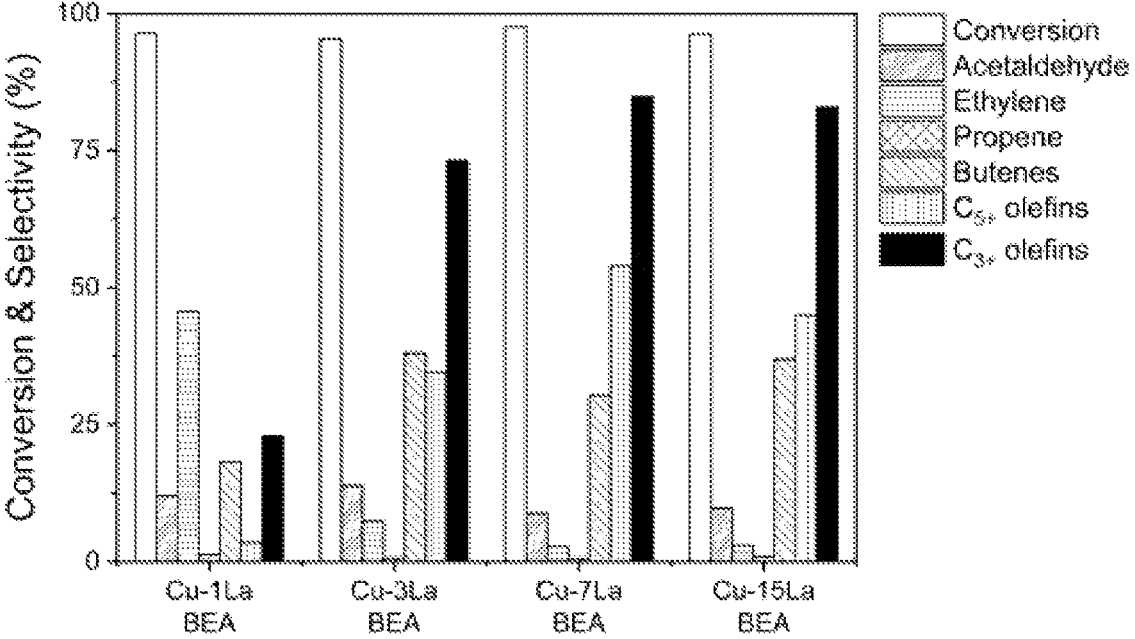
FIG. 3. Graph showing ethanol conversion and product selectivities over four Cu—Ce/Beta catalysts at 623 K, 101.3 kPa, WHSV=0.52 h$^{-1}$, 7.1 kPa ethanol balanced with H$_2$.

Both acetaldehyde and ethylene selectivities decreased as the La loading increased from 1 wt % to 15 wt %. The ethylene selectivity was as low as 3% when the La loading was 15 wt %. Propene selectivity was observed to be below 2% over all these catalysts. Butene selectivity was maximized at 38% on Cu-3La/Beta, while maximum C$_{5+}$ olefins (54%) was observed over Cu-7La/Beta. The maximum C$_{3+}$ olefin selectivity was 85% with primarily butenes and C$_{5+}$ olefins. The results are graphically presented in FIG. 3.

Example 3. Cu/Silica+7La/Beta Catalyst for Ethanol Conversion to Olefins

The DeAl-Beta support was prepared using the same procedure as Example 1. The metal loading procedure for La/Beta was also similar to Example 1 except for the use of lanthanum nitrate hexahydrate in place of cerium nitrate hexahydrate. The nominal La loading was 7 wt %. Cu-silica (1 wt %) was synthesized using the same method (copper nitrate trihydrate as Cu source) on commercially available silica (Sigma-Aldrich, pore size 1.5 nm, pore volume 1.15 cm$^3$ g$^{-1}$). These two catalysts were physically mixed using a weight ratio of 1:1, and tested in the same reactor setup and under the same conditions as the Cu—Ce/Beta catalysts in Example 1.

Catalytic Performance

The physical mixture of Cu/Silica+7La/Beta catalyst was tested at temperatures of 623 K to 673 K. As the temperature increased, ethanol conversion increased from 92% to 100%. Acetaldehyde selectivity dropped significantly from 24% to 3.9%. Both ethylene and propene selectivities were much lower than 10%. Maximum butene selectivity and C$_{5+}$ olefin selectivity were 52% and 39%, respectively. C$_{3+}$ selectivity reached a maximum (87%) at 673 K. The results are shown in Table 3 below.

TABLE 3

| | | | | | | | | | |
|---|---|---|---|---|---|---|---|---|---|
| Ethanol conversion and product selectivities over Cu/Silica + 7La/Beta catalyst at different reaction temperatures | | | | | | | | | |
| Temp. | WHSV | | | Selectivity | | | | | |
| (K) | (h$^{-1}$) | Conv. | Acetaldehyde | C$_2$$^-$ | C$_3$$^-$ | C$_4$$^-$ | Butadiene | C$_{5+}$$^-$ | C$_{3+}$$^-$ |
| 623 | 0.53 | 92 | 24 | 1.9 | 0.4 | 22 | 0.1 | 39.2 | 61.6 |
| 648 | 0.53 | 97 | 10 | 4.4 | 2.9 | 51 | 1.0 | 27.0 | 80.5 |
| 673 | 0.53 | 100 | 3.9 | 6.0 | 4.0 | 52 | 0.3 | 31.2 | 87.0 |

Reaction conditions: 101.3 kPa, WHSV = 0.52 h$^{-1}$, 7.1 kPa ethanol balanced with H$_2$.

Figure 2:
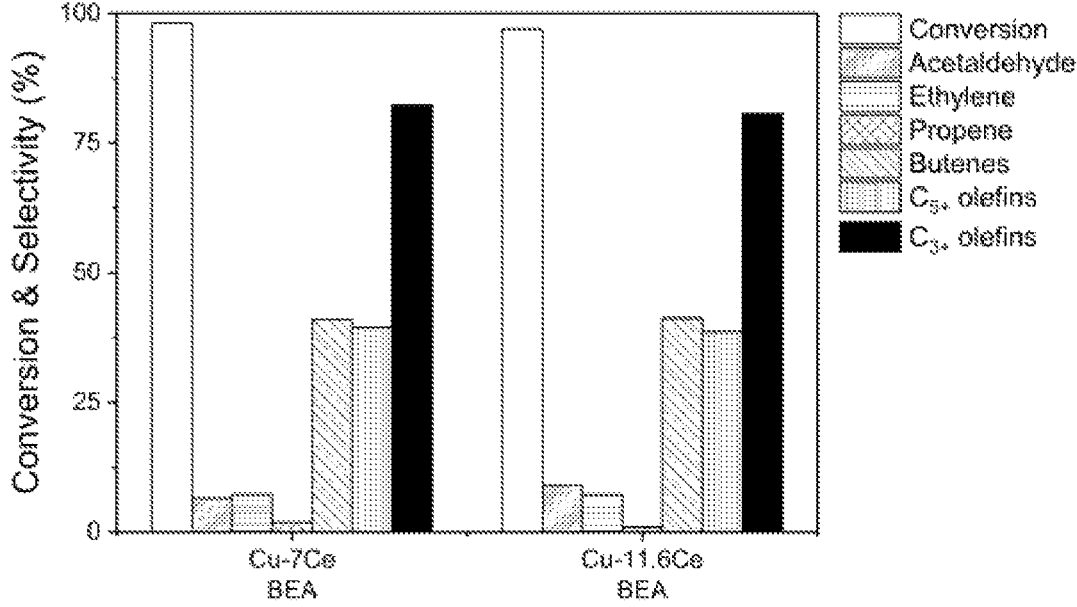
FIG. 2. Graph showing ethanol conversion and product selectivities over Cu-7Ce/Beta catalyst and Cu-11.6Ce/Beta catalyst at 623 K, 101.3 kPa, WHSV=0.52 h$^{-1}$, 7.1 kPa ethanol balanced with H$_2$.

Beta, respectively. Small amounts of acetaldehyde and ethylene were also observed. The results are graphically presented in FIG. 2.

Example 2. Cu—La/Beta Catalyst for Ethanol Conversion to Olefins

The DeAl-Beta support was prepared using the same procedure as Example 1. The metal loading procedure is also similar except for the use of lanthanum nitrate hexahydrate in place of cerium nitrate hexahydrate. The nominal loading of Cu was 1 wt %, while the La loading was varied at 1, 3, 7, and 15 wt % for the catalysts Cu-1La/Beta, Cu-3La/Beta, Cu-7La/Beta, and Cu-15La/Beta, respectively. These catalysts were tested in the same reactor setup and under the same conditions as the Cu—Ce/Beta catalysts in Example 1.

Ethanol conversions over all these catalysts were above 95%. Over each catalyst, the observed products include acetaldehyde, ethylene, propene, butenes and C$_{5+}$ olefins.

Example 4. Cu/Silica+Zn-La/Beta Catalyst for Ethanol Conversion to Olefins

The DeAl-Beta support was prepared using the same procedure as Example 1. The metal loading procedure for Zn—La/Beta was similar to Example 1 except for the use of zinc nitrate hexahydrate and lanthanum nitrate hexahydrate in place of cerium nitrate hexahydrate. The nominal Zn and La loadings were 2 wt % and 7 wt %, respectively. Cu-silica (1 wt %) was synthesized using same method (copper nitrate trihydrate as Cu source) on commercially available silica (Sigma-Aldrich, pore size 1.5 nm, pore volume 1.15 cm$^3$ g$^{-1}$). These two catalysts were physically mixed using a weight ratio of 1:1, and tested in the same reactor setup and under the same conditions as the Cu—Ce/Beta catalysts in Example 1.

Catalytic Performance

The physical mixture of Cu/Silica+Zn-La/Beta catalyst was tested at temperatures of 623 K to 673 K. As temperature increased, ethanol conversion increased from 94% to 100%. Acetaldehyde selectivity dropped significantly from 18% to 3.1%. Both ethylene and propene selectivities were much lower than 10%. Maximum butene selectivity and $C_{5+}$ olefin selectivity were 45% and 44%, respectively. $C_{3+}$ selectivity reached a maximum (86%) at 673 K. The results are shown in Table 4 below.

TABLE 4

| Ethanol conversion and product selectivities over Cu/Silica + Zn—La/Beta catalyst at different reaction temperatures | | | | | | | | | |
|---|---|---|---|---|---|---|---|---|---|
| Temp. | WHSV | | Selectivity | | | | | | |
| (K) | $(h^{-1})$ | Conv. | Acetaldehyde | $C_2^-$ | $C_3^-$ | $C_4^-$ | Butadiene | $C_{5+}^-$ | $C_{3+}^-$ |
| 623 | 0.52 | 94 | 18 | 3.0 | 0.9 | 24 | 0.1 | 44 | 69 |
| 648 | 0.52 | 98 | 8.4 | 5.4 | 5.5 | 42 | 2.7 | 32 | 79 |
| 673 | 0.52 | 100 | 3.1 | 7.3 | 6.8 | 45 | 0.8 | 34 | 86 |

Reaction conditions: 101.3 kPa, WHSV = 0.52 $h^{-1}$, 7.1 kPa ethanol balanced with $H_2$.

Example 5. Cu—Zn—La/Beta Catalyst for Ethanol Conversion to Olefins

The DeAl-Beta support was prepared using the same procedure as Example 1. The metal loading procedure for Cu—Zn—La/Beta was also similar to Example 1 except for the use of zinc nitrate hexahydrate and lanthanum nitrate hexahydrate in place of cerium nitrate hexahydrate. The nominal Cu, Zn and La loadings were 1 wt %, 2 wt % and 7 wt %, respectively. The catalyst was tested in the same reactor setup and under same conditions as Cu—Ce/Beta catalysts in Example 1.
Catalytic Performance This Cu—Zn—La/Beta catalyst was tested at temperatures of 573 K to 673 K. As the temperature increased, ethanol conversion increased from 82% to 99%. Acetaldehyde selectivity dropped significantly from 18% to 4.9%. Both ethylene and propene selectivities were much lower than 10%. Maximum butene selectivity and $C_{5+}$ olefin selectivity were 38% and 49%, respectively. $C_{3+}$ selectivity reached a maximum (88%) at 673 K. The results are shown in Table 5 below.

TABLE 5

| Ethanol conversion and product selectivities over Cu—Zn—La/Beta catalyst at different reaction temperatures | | | | | | | | | |
|---|---|---|---|---|---|---|---|---|---|
| Temp. | WHSV | | Selectivity | | | | | | |
| (K) | $(h^{-1})$ | Conv. | Acetaldehyde | $C_2^-$ | $C_3^-$ | $C_4^-$ | Butadiene | $C_{5+}^-$ | $C_{3+}^-$ |
| 573 | 0.52 | 82 | 18 | 1.7 | 0.8 | 23 | 0.1 | 47 | 71 |
| 623 | 0.52 | 96 | 11 | 6.1 | 1.4 | 33 | 0.1 | 44 | 79 |
| 673 | 0.52 | 99 | 4.9 | 4.2 | 1.8 | 38 | 0.0 | 49 | 88 |

Reaction conditions: 101.3 kPa, WHSV = 0.52 $h^{-1}$, 7.1 kPa ethanol balanced with $H_2$.
Example 6. Cu-La/Beta Catalyst for Ethanol Conversion to 1,3-Butadiene The DeAl-Beta support was prepared using the same procedure as Example 1. The metal loading procedure for Cu—La/Beta was also similar to Example 1 except for the use of lanthanum nitrate hexahydrate in place of cerium nitrate hexahydrate. The nominal Cu and La loadings were 1 wt % and 7 wt %, respectively. The catalyst was tested in the same reactor setup and under similar reaction conditions as Cu—Ce/Beta catalysts in Example 1 except using inert helium instead of hydrogen during the reaction.

Catalytic Performance

Figure 4:
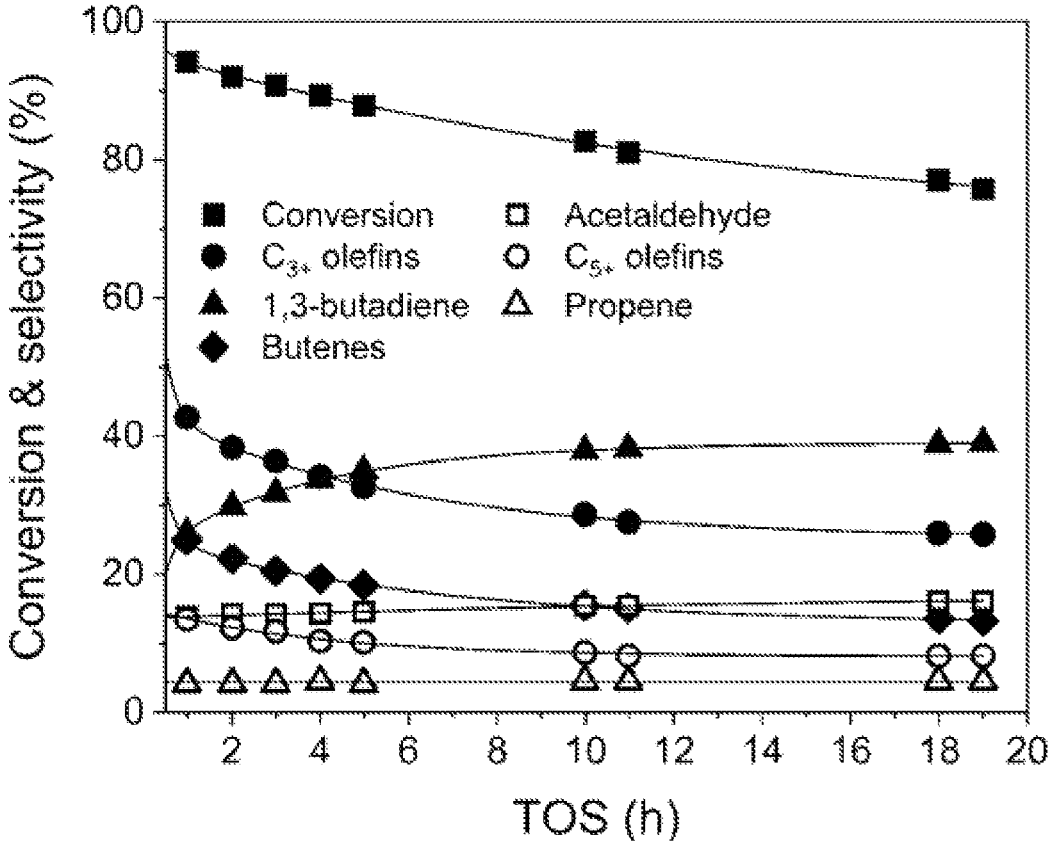
FIG. 4. Graph showing ethanol conversion and product selectivities over Cu—La/Beta catalyst at 623 K, 101.3 kPa, WHSV=0.52 h$^{-1}$, 7.1 kPa ethanol balanced with He.

This Cu—La/Beta catalyst was tested at 623 K under inert environment. Instead of $C_{3+}$ olefins as the major product, 1,3-butadiene was produced in significantly amount (approaching 40% selectivity). The results are graphically presented in FIG. 4.

Example 7. Cu—Zn—La-Beta Catalyst for ABE (Acetone, 1-Butanol and Ethanol) Conversion to Olefins H-Beta Dealumination H-BEA (SAR=11.5) was obtained by calcining $NH_4$-Beta (CP814E, Zeolyst) under 823 K under 1.7 $cm^3$ $g^{-1}$cat $s^{-1}$ air for 12 h. 10 g H-Beta was mixed with 250 mL nitric acid (69% to 70%) in a sealed container at 353 K with 500 rpm stirring for 16 h. The solid was centrifuged and washed with DI water until pH is close to 9. The washed powder was dried under 353 K in oven overnight to remove the remaining water and acid. The sample was labeled as DeAl-Beta as the support for metal loading.
Loading of Cu, Zn and La DeAl-Beta was mixed with copper nitrate trihydrate, lanthanum nitrate hexahydrate, and zinc hexahydrate in the mortar and ground for 20 min. The mixed powder was homogeneous light green with no blue dots. The mixture was calcinated to 823 K with 1 K/min ramping rate and held for 6 h under 13.3 $cm^3$ $g^{-1}$cat $s^{-1}$ air to allow a complete decomposition of metal precursors and homogeneous distribution of metal species. The catalyst has nominal loadings of 1 wt % Cu, 2 wt % Zn and 7 wt % La.
Catalytic Performance Test The reaction was carried out in a tubular quartz reactor with a fixed-bed configuration in a vertical tubular furnace. Typically, 0.3 g catalyst was treated in situ by heating at 5 K $min^{-1}$ to 673 K and for 1 h under 1.2 $cm^3$ $g^{-1}$cat $s^{-1}$ He to remove adsorbed species. After cooling down to 623 K, the catalyst was reduced under 1. $cm^3$ $g^{-1}$cat $s^{-1}$ pure $H_2$ for 30 min. Flow rates of He and $H_2$ were controlled using mass flow controllers. ABE mixture (30 wt % acetone, 60 wt % butanol and 10 wt % ethanol) was delivered by syringe pumps and was evaporated inside the ⅛ inches stainless steel transfer lines. The types and concentrations of the reactants and products in the stream were measured by a gas-chromatograph with thermal conductivity detector (TCD) and a flame ionization detector (FID). A gas chromatograph mass-spectrometer (GC-MS) was used to determine the peak position of reactants and products.

Catalytic Performance

Figure 5:
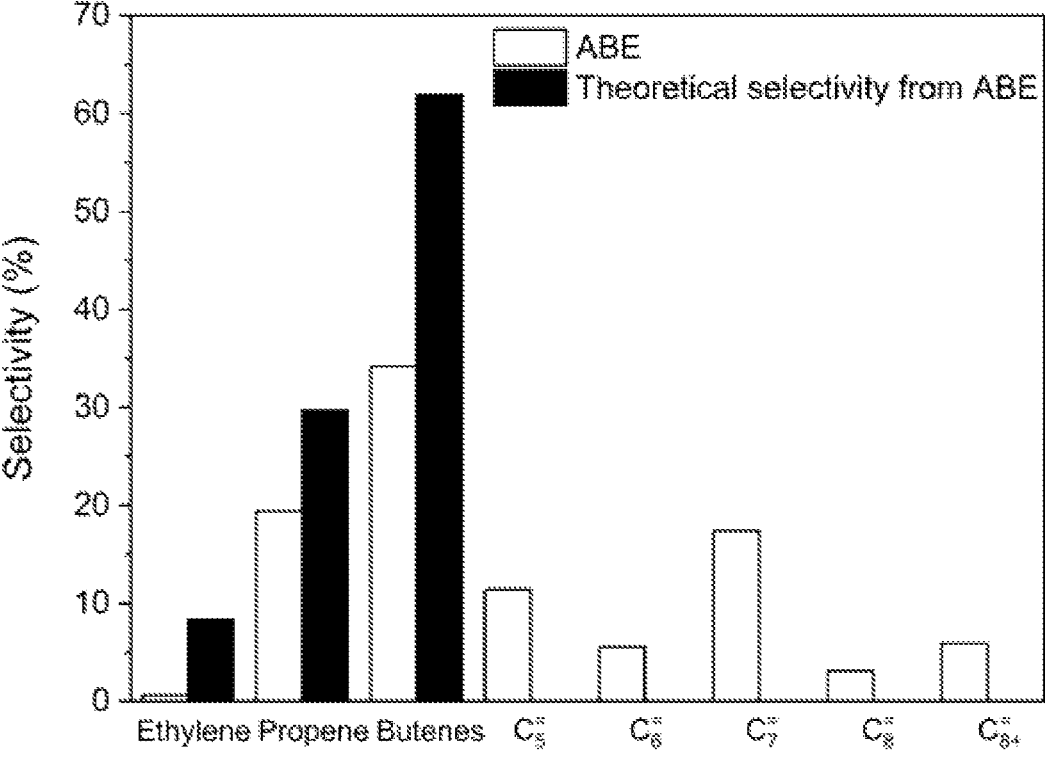
FIG. 5. Graph showing theoretical and actual selectivities achieved by conversion of ABE fermentation stream over Cu—Zn—La/Beta catalyst at 623 K, WHSV=0.54 h$^{-1}$, 2.70 kPa 1-butanol, 1.73 kPa acetone, and 0.728 kPa ethanol balanced with 96.1 kPa H$_2$.

Total carbon conversion of ABE mixture was 99.8%. Theoretical selectivities from ABE are 8.3% ethylene, 29.7% propene and 62.0% butenes, respectively, assuming ethanol was converted to ethylene, acetone was upgraded to propene, and 1-butanol was transformed to butenes. In the experiment, a significant decrease of all three olefins, particularly ethylene, in comparison with the theoretical selectivities was observed. At the same time, larger olefins from pentene to $C_{8+}$ olefins were observed due to potential condensation among acetone, 1-butanol and ethanol. The results are graphically presented in FIG. 5.

Example 8. Cu/Silica+Zn-La/Beta Catalyst for Ethanol/1-Butanol Conversion to Olefins H-Beta Dealumination H-BEA (SAR=11.5) was obtained by calcinating NH$_4$-Beta (CP814E, Zeolyst) under 823 K under 1.7 cm$^3$ g$^{-1}$cat s$^{-1}$ air for 12 h. 10 g H-Beta was mixed with 250 mL nitric acid (69% to 70%) in a sealed container at 353 K with 500 rpm stirring for 16 h. The solid was centrifuged and washed with DI water until pH is close to 9. The washed powder was dried under 353 K in an oven overnight to remove the remaining water and acid. The sample was labeled as DeAl-Beta as the support for metal loading.

Loading of Cu and La

DeAl-Beta was mixed with lanthanum nitrate hexahydrate and zinc nitrate hexahydrate in the mortar and ground for 20 min. The mixture was calcinated to 823 K with 1 K/min ramping rate and held for 6 h under 13.3 cm$^3$ g$^{-1}$cat s$^{-1}$ air to allow a complete decomposition of metal precursors and homogeneous distribution of metal species. Cu/silica was synthesized using the same method (copper nitrate trihydrate as Cu source) on commercially available silica (Sigma-Aldrich, pore size 1.5 nm, pore volume 1.15 cm$^3$ g$^{-1}$). Cu/silica contains 1 wt % Cu and La-Beta has 7 wt % La and 2 wt % Zn.

Catalytic Performance Test

The reaction was carried out in a tubular quartz reactor with a fixed-bed configuration in a vertical tubular furnace. Typically, 0.3 g catalyst (physical mixture with Cu/silica to Zn—La/Beta weight ratio of 1:1) was treated in situ by heating at 5 K min$^{-1}$ to 673 K and for 1 h under 1.2 cm$^3$ g$^{-1}$cat s$^{-1}$ He to remove adsorbed species before the test. After cooling down to 623 K, the catalyst was reduced under 1.2 cm$^3$ g$^{-1}$cat s$^{-1}$ pure H$_2$ for 30 min. Flow rates of He and H$_2$ were set using mass flow controllers. 1-Butanol and butanol-ethanol mixture (61.7 wt % butanol and 38.3 wt % ethanol) were delivered by syringe pumps and were evaporated inside the ⅛ inches stainless steel transfer lines. The types and concentration of reactants and products in the stream were measured by a gas-chromatograph with thermal conductivity detector (TCD) and a flame ionization detector (FID). A gas chromatograph mass-spectrometer (GC-MS) was used to determine the peak position of reactants and products.

Catalytic Performance

Figure 6:
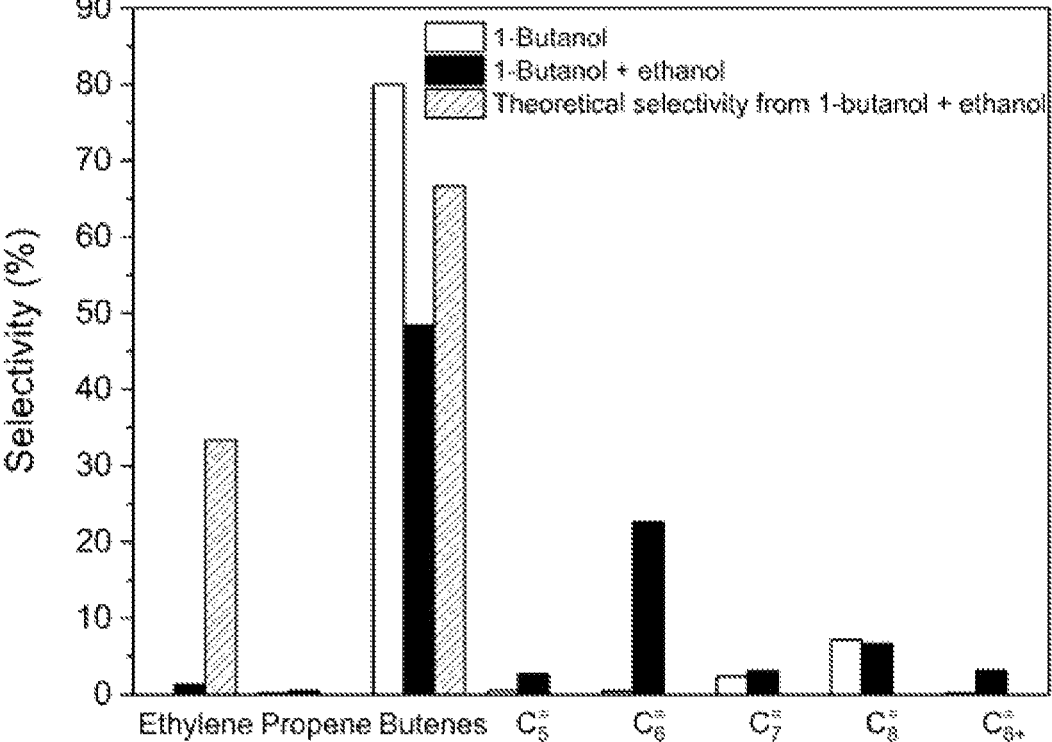
FIG. 6. Graph showing selectivities for conversion of 1-butanol, and theoretical and actual product selectivities achieved by conversion of a mixture of 1-butanol and ethanol over Cu/silica+Zn-La/Beta. For 1-butanol feed, the reaction was carried out at 623 K, WHSV=0.54 h⁻¹, 4.59 kPa 1-butanol and 96.7 kPa $H_2$. For the mixture feed, the reaction was performed at 623 K, 101.3 kPa, WHSV=0.44 h⁻¹, 2.29 kPa 1-butanol and 2.30 kPa ethanol balanced with 96.7 kPa $H_2$.

When only feeding 1-butanol, the primary product was butenes from the dehydration reaction along with minor $C_7$ and $C_8$ olefins. Theoretical selectivities from 1-butanol and ethanol are 33% ethylene and 67% butenes, respectively, assuming ethanol is converted to ethylene and 1-butanol is transformed to butenes. In the experiment, a significant decrease of both olefins, particularly ethylene, in comparison with the theoretical selectivities was observed. Instead, larger olefins from hexene to $C_{8+}$ olefins were observed due to potential condensation of ethanol and 1-butanol. The results are graphically presented in FIG. 6.

While there have been shown and described what are at present considered the preferred embodiments of the invention, those skilled in the art may make various changes and modifications which remain within the scope of the invention defined by the appended claims.

What is claimed is:

1. A method for converting an alcohol to an olefin fraction comprising 1,3-butadiene, the method comprising contacting the alcohol with a catalyst to result in direct conversion of said alcohol to said olefin fraction comprising 1,3-butadiene;

wherein said catalyst comprises the following components:

(a) support particles comprising silicon (Si) and oxygen (O);

(b) at least one of copper and silver residing on and/or incorporated into said support particles; and (c) at least one lanthanide element comprising lanthanum residing on and/or incorporated into said support particles.

2. The method of claim 1, wherein paraffins are optionally produced along with the olefin fraction in an amount of no more than 3 vol %.

3. The method of claim 1, wherein aromatics are optionally produced along with the olefin fraction in an amount of no more than 2 vol %.

4. The method of claim 1, wherein butenes are produced in an amount of less than 50 vol % in said olefin fraction.

5. The method of claim 1, wherein olefins containing at least five carbon atoms are present in said olefin fraction in an amount of less than 50 vol %.

6. The method of claim 1, wherein said alcohol has one to four carbon atoms.

7. The method of claim 1, wherein said alcohol comprises ethanol.

8. The method of claim 1, wherein said alcohol is in aqueous solution in a concentration of no more than 50 vol %.

9. The method of claim 1, wherein said alcohol is a component of a fermentation stream when contacted with said catalyst.

10. The method of claim 1, wherein said alcohol is a component of an acetone-butanol-ethanol (ABE) fermentation stream when contacted with said catalyst.

11. The method of claim 1, wherein the 1,3-butadiene is produced in a selectivity of at least 35%.

12. The method of claim 1, wherein ethylene is produced in an amount of less than 50 vol % in said olefin fraction.

13. The method of claim 1, wherein propene is produced in an amount of less than 50 vol % in said olefin fraction.

14. The method of claim 1, wherein said support particles comprise beta zeolite.

15. The method of claim 1, wherein said catalyst further comprises: (d) zinc atoms residing on and/or incorporated into said support particles.

* * * * *